(12) United States Patent
Dehé et al.

(10) Patent No.: US 11,726,029 B2
(45) Date of Patent: Aug. 15, 2023

(54) MODULATION OF A MOVABLE IR EMITTER THROUGH A DIAPHRAGM STRUCTURE

(71) Applicant: Hahn-Schickard-Gesellschaft für angewandte Forschung e. V., Villingen-Schwenningen (DE)

(72) Inventors: Alfons Dehé, Reutlingen (DE); Achim Bittner, Heilbronn (DE); Daniel Biesinger, Villingen-Schwenningen (DE)

(73) Assignee: Hahn-Schickard-Gesellschaft für angewandte Forschung e. V, Villingen-Schwenningen (DE)

( * ) Notice: Subject to any disclaimer, the term of this patent is extended or adjusted under 35 U.S.C. 154(b) by 353 days.

(21) Appl. No.: 17/250,856

(22) PCT Filed: Sep. 13, 2019

(86) PCT No.: PCT/EP2019/074514
§ 371 (c)(1),
(2) Date: Mar. 12, 2021

(87) PCT Pub. No.: WO2020/053400
PCT Pub. Date: Mar. 19, 2020

(65) Prior Publication Data
US 2022/0057320 A1    Feb. 24, 2022

(30) Foreign Application Priority Data
Sep. 13, 2018 (EP) .................... 18194207

(51) Int. Cl.
*G01N 21/17* (2006.01)
*G01N 33/00* (2006.01)
*G02B 26/04* (2006.01)

(52) U.S. Cl.
CPC ..... *G01N 21/1702* (2013.01); *G01N 33/0027* (2013.01); *G02B 26/04* (2013.01); *G01N 2021/1704* (2013.01)

(58) Field of Classification Search
CPC .......... G01N 21/1702; G01N 33/0027; G01N 2021/1704; G02B 26/04; G01J 3/108; G01J 3/0237
See application file for complete search history.

(56) References Cited

U.S. PATENT DOCUMENTS 4,117,177 A * 9/1978 Schlafer ................. B23K 26/18
427/272
6,407,400 B1    6/2002 Durocher
(Continued)

FOREIGN PATENT DOCUMENTS

DE    195 26 352 A1    7/1997
GB    2502520 A    12/2013

OTHER PUBLICATIONS

International Search Report in PCT/EP2019/074514, dated Dec. 20, 2019 (English Translation).

*Primary Examiner* — Suman K Nath
(74) *Attorney, Agent, or Firm* — Knobbe, Martens, Olson & Bear, LLP (57) ABSTRACT

The invention relates to a modulatable infrared emitter comprising an aperture structure, a structured micro-heating element, and an actuator, wherein the aperture structure and the structured micro-heating element are movable relative to each other in parallel planes by means of the actuator to modulate the intensity of emitted infrared radiation. The invention further relates to methods of manufacturing the infrared emitter, a method of modulating emission of infrared radiation using the infrared emitter, and preferred uses of the infrared emitter. In further aspects the invention relates
(Continued)

to a system comprising the infrared emitter and a control device for regulating the actuator.

20 Claims, 3 Drawing Sheets

(56) References Cited

U.S. PATENT DOCUMENTS

2015/0314732 A1* 11/2015 Lynam .................... B60Q 1/26
340/425.5
2020/0152490 A1* 5/2020 Yanagisawa ........ H01L 21/6719

* cited by examiner

MODULATION OF A MOVABLE IR EMITTER THROUGH A DIAPHRAGM STRUCTURE

DESCRIPTION

The invention relates to a modulatable infrared emitter comprising an aperture structure, a structured micro-heating element, and an actuator, wherein the aperture structure and the structured micro-heating element are movable relative to each other in parallel planes by means of the actuator to modulate the intensity of emitted infrared radiation. The invention further relates to methods of manufacturing the infrared emitter, methods of modulating emission of infrared red radiation using the infrared emitter, and preferred uses of the infrared emitter. In further aspects the invention relates to a system comprising the infrared emitter and a control device for regulating the actuator.

BACKGROUND AND STATE OF THE ART

Modulatable infrared emitters (IR emitters) are relevant for a variety of applications in spectroscopy. In particular, the spectroscopy of gases is often performed with the aid of infrared radiation, which at certain frequencies triggers vibrations of the molecules detectable as absorption lines in the spectrum.

Photoacoustic spectroscopy is often used, employing intensity-modulated infrared radiation with frequencies in the absorption spectrum of a molecule to be detected in a gas. If this molecule is present in the beam path, modulated absorption takes place, leading to heating and cooling processes whose time scales reflect the modulation frequency of the radiation. The heating and cooling processes lead to expansions and contractions of the gas, causing acoustic waves at the modulation frequency. Said acoustic waves can subsequently be measured by acoustic detectors (microphones) or flow sensors.

Photoacoustic spectroscopy allows the detection of very fine concentrations of gases and has a variety of applications. An example is the detection of $CO_2$, which takes an important role in research and air conditioning technology. The concentration of exhaust gases in the air may for instance also be measured in this way. Military applications in which smallest concentrations of toxic gas can be detected may also be relevant.

Various emitters are used as radiation sources for the above applications, with different advantages and disadvantages. For example, narrowband laser sources in the infrared range can be used. These allow the use of high radiation intensities and can be high-frequency modulated with standard components, e.g. for photoacoustic spectroscopy. However, due to the narrow spectrum of the laser, only molecules with a matching absorption spectrum can be detected. Lasers are also relatively expensive. If a detect of a number of different molecules is desired, a corresponding number of lasers must be used.

Thermal, broadband emitters are also known. These have the advantage of a wide spectrum and often low cost. However, the modulation frequency of these emitters is limited, direct modulation by varying the current supply is slow due to thermal time constants and significantly degrades device life. Slow modulation often results in a measurement with a poor signal-to-noise ratio due to the inherent noise of the detection components. External modulation through the use of spinning chopper wheels is faster, but the setup is costly and not as compact and robust as would be desirable for many applications. Also, modulation bandwidths are limited and varying the rotation speed of the chopper is cumbersome due to inertias.

Other approaches to modulating IR emitters are known in the prior art.

DE 195 26 352 A1 has set itself the task of improving the modulation of the beam path in nondispersive infrared gas analyzers compared to known rotating aperture wheels. To this end, DE 195 26 352 A1 proposes to rotate an emitter about an axis perpendicular to the beam axis and to modulate the emitter by means of one or more apertures. In one embodiment, a rod-shaped radiator at the focal point of a reflector is proposed, which is modulated in phase opposition by means of two rotating apertures offset by 90°. Thus, a fast rotation of the IR radiator itself, which is mounted on a shaft, is necessary to achieve a high-frequency modulation. This increases the construction effort and makes a compact arrangement more difficult.

From GB 2502520 A an electro-optical simulation of light sources with a time-varying light intensity profile as defense signals is known. A homogeneous arc lamp with a broad spectrum in the infrared range is used as the radiation source. To modulate the light intensity, the use of one or more templates with a plurality of transmission ranges is proposed. In one embodiment, the stencil is tilted with respect to the light source to obscure the transparency regions as seen by the light source. Here, the necessary angle of inclination depends on the thickness of the stencil. In another embodiment, two stencils are shifted against each other in order to cover the transmission areas from the point of view of the arc lamp. The modulation is intended to provide a simulation of a light source that allows a rapid rise and a gradual decay. Even in an open position, a substantial amount of light is absorbed by the non-transmission regions of the templates, reducing the maximum emission amplitude.

U.S. Pat. No. 6,407,400 B1 relates to a modulation of infrared light sources as a defense measure for heat-seeking missiles. The modulation means proposed are a collection element, a stator, and two rotors comprising alternating opaque and translucent material. The construction method of U.S. Pat. No. 6,407,400 B1 requires precise tuning of the rotating elements. In addition, even in the case of U.S. Pat. No. 6,407,400 B1, a substantial amount of infrared light is always absorbed by the non-transmissive during momentary open positions, reducing the maximum emission amplitude.

These approaches to providing modulated infrared emitters are therefore not as compact, robust and energy-efficient as would be desirable for many applications. Today, microsystems technology is used to manufacture compact mechanical-electronic devices in many fields of application. The microsystems (microelectromechanical systems, or MEMS) that can be manufactured in this way are very compact (micrometer range) while offering outstanding functionality and ever lower manufacturing costs. For example, DE 10 2017 206 183 A1 describes fast and compact comb drives as MEMS actuators.

A use of MEMS technology to modulate a thermally generated infrared radiation is not known from the prior art.

OBJECTIVE OF THE INVENTION

It is an objective of the invention to provide a modulatable infrared emitter as well as a method for generating modulated infrared radiation without the disadvantages of the prior art. In particular, it was an objective of the invention to provide a high-frequency and variably modulatable infrared emitter which can emit a broad spectrum of infrared radiation in a modulated manner and at the same time is characterized by a simple, low-cost compact design.

SUMMARY OF THE INVENTION

The objective is solved by the features of the independent claims. Advantageous embodiments of the invention are described in the dependent claims.

In a first aspect, the invention relates to a modulatable infrared emitter comprising.
an aperture structure,
a structured micro-heating element and
an actuator,
wherein the micro-heating element has heatable and non-heatable regions in a first plane, the aperture structure has transmissive (transparent) and non-transmissive (opaque) regions for infrared radiation in a second plane, the two planes being parallel to each other, the aperture structure and the micro-heating element are movable in the parallel planes relative to each other, and the actuator is configured for relative movement of the aperture structure and the micro-heating element between at least a first and a second position, such that an extinction ratio of at least 2 is achievable for the infrared radiation emittable from the micro-heating element through the aperture structure between the first and the second position. To this end the arrangement or dimensioning of the heatable and non-heatable regions of the structured micro-heating element and the arrangement or dimensioning of the transmissive and non-transmissive regions r of the aperture structure are preferably matched to one another in such a way that, in the first position, the IR radiation emittable by the heatable regions is predominantly absorbed and/or reflected by the non-transmissive regions of the aperture structure, while, in the second position, the IR radiation emittable by the heatable regions predominantly radiates through the transmissive regions of the aperture structure.

Due to the movability of the aperture structure relative to the structured heating element, a modulation of the intensity of the emitted infrared radiation can be achieved in a particularly fast and simple manner. In contrast to known intensity modulations in infrared emitters by varying the current supply, the modulation according to the invention is not limited by thermal time constants. Rather, MEMS actuators can be used to achieve modulation frequencies well above 100 Hz. Such modulation frequencies are particularly advantageous for photoacoustic spectroscopy. However, the modulatable infrared emitter is suitable for any application where fast and reliable modulation of infrared radiation is required.

Primarily, the modulatable infrared emitter is a device that emits electromagnetic radiation. This radiation preferably exhibits a wavelength range in the infrared (IR) region, particularly between about 700 nanometers (nm) and 1 millimeter (mm) wavelength. The corresponding frequency of the emitted radiation may be in the range between about 300 gigahertz (GHz) to 400 terahertz (THz). The spectrum may just as preferably be represented in terms of the wavenumber m−1 or cm−1, as it is common in the field of spectroscopy. A person skilled in the art knows how to convert to these units. The term emitter preferably refers to the device comprising the radiation source, which is represented by the micro-heating element, and an aperture structure, which enables the modulation of the infrared radiation by relative movements with respect to the micro-heating element.

In particular, the spectrum is selected to correspond to the preferred field of application of the emitter, namely infrared spectroscopy and especially photoacoustic spectroscopy. In particular, the vibrational excitation of the gas molecules to be analyzed and/or detected is preferred, which correspond to a preferred spectral range depending on the gas molecules. For example, a spectral range of the IR emitter encompassing a wavelength of about 2.4 micrometers (μm) is suitable for the excitation of $CO_2$ molecules. Particularly preferred wavelength ranges of infrared radiation are 700 nm to 10 μm, preferably 1 to 5 μm, especially preferably 2 μm to 3 μm.

The radiation can be emitted isotropically, i.e. uniformly in all spatial directions starting from the emitter. In this context, uniform means preferably with the same intensity of the radiation. Intensity is defined in particular as area power density and preferably has the unit watts per square meter or abbreviated $W/m^2$. However, as opposed to isotropic emission of the radiation, it is preferred that the radiation is bundled in the form of a beam oriented along a preferred direction in the form of a degree. Since the radiation of an emitter, especially without additional components, typically diverges and can preferably be described with respect to the emitting surface, e.g., by Lambert's law, additional components such as lenses can be integrated in the emitter or attached externally to provide for bundling or collimation of the beam. A person skilled in the art knows how to shape the emission profile of the radiation source by designing the radiation source as well as by using additional components to result in a desired beam profile as well as a desired beam direction. Preferably, the modulatable IR emitter may comprise only the actual radiation source without additional lenses as well as a system comprising radiation source and at least one lens for collimation of the beam. In the further course, the term beam shall describe the preferably bundled part of the radiation along the preferred beam direction of the emitter, which is emitted by the emitter, wherein particular the portions of greatest intensity along said direction define the beam. For the radiation or beam propagating between the micro-heating element and the aperture structure in the following the terms unmodulated radiation or the unmodulated beam will be used to allow for a distinction of the beam outside the IR emitter.

The emitter is modulatable, which means that the intensity of the emitted radiation, preferably the intensity of the beam can be changed in a controllable manner over time. The modulation shall preferably cause a temporal change of the intensity as a measurable quantity. This means, for example, that there is a difference in intensity over time between the weakest intensity measured within the measurement period and the strongest intensity measured within the same period that is greater than the sensitivity of an instrument typically used for the radiation spectrum and application to measure or determine intensity. Preferably, the difference is significantly greater than a factor of 2 between the strongest and weakest adjustable intensities. A modulatable infrared emitter has a variety of applications. In terms of relevant applications infrared spectroscopy and especially photoacoustic spectroscopy are to be mentioned.

A thermal emitter in the form of a micro-heating element is provided to generate the infrared radiation. A micro-heating element is preferably understood to be a heating element with dimensions of the order of micrometers (μm). Here, the heating element comprises a heatable layer of a conductive material which produces joule heat when an electric current flows through the material. The heat produced preferably exhibits a dependence on the ohmic resistance of the element and the square of the current or the square of the applied voltage and the inverse ohmic resistance, depending on whether a current or voltage source is used. In a state of equilibrium, the heat produced is equal to the heat losses due to thermal conduction, convection and thermal radiation (synonymous: infrared radiation) emitted at the external interfaces of the heatable layer through which the current flows. As is known to the person skilled in the art, the heat produced causes, i.a. thermal radiation, in particular by thermal movement of particles, which results, for example, in an acceleration of charge carriers and/or oscillating dipole moments. Thus, infrared radiation can be specifically generated by a current-carrying heatable layer. The heatable layer is preferably made of metal, for example tungsten or platinum. By applying a suitable voltage, the resulting current flow leads to the generation of joule heat and ultimately infrared radiation. The radiation spectrum can preferably be described approximately by Planck's radiation law, wherein the person skilled in the art is aware of the differences between an actual heatable layer and a black body, for example, the emissivity or the actual deviation from a thermal equilibrium of the body. Despite these deviations, the generated spectrum and its intensity is essentially described by the temperature and the radiating area according to Planck's radiation law. Thus, a skilled person can achieve a preferred spectrum with a preferred intensity distribution by specific design of the micro-heating element. For this purpose, in addition to the material and the geometric design of the heating element, the electrical energy provided, a surface treatment of the radiating interface, and the magnitude of the heat losses of the heating element in addition to the thermal radiation are preferably decisive. The magnitude of these heat losses is determined, for example, by the thermal conductivity between the heating element and the adjacent materials and/or fluids as well as their heat capacity and the size of the interface(s).

The structured micro-heating element is preferably characterized by a two-dimensional plane, the first plane, in which, heatable and non-heatable regions are present. Heatable regions are regions comprising a heatable layer of a conductive material as described above. A non-heatable region is preferably defined by not being a heatable region and being adjacent to a heatable region or between two heatable regions. When a current is applied, infrared radiation is preferably emitted from the heatable regions in the direction of emission, while this is not the case for the non-heatable regions.

Preferably, the heatable and non-heatable regions within the first plane are arranged substantially along a line. For example, the micro-heating element could comprise a surface of a cuboid substrate that constitutes the first plane. On this surface, in the form of electrically contacted strips (e.g., coatings), the heatable regions may be deposited. These could be oriented, for example, perpendicular to the long side of the cuboid surface. Between these strips, there may be essentially strip-shaped, non-heatable regions. It may be preferred that the heatable strips are shorter than the short side of the cuboid surface, so that all non-heatable regions are connected along one long side of the cuboid surface. Even though the non-heatable regions form a connected surface in this embodiment, there are multiple non-heatable regions for the purposes of the invention. In particular, heatable and non-heatable regions alternate along the centerline of the cuboid, which, relative to an appropriately selected aperture structure, allows for the modulation according to the invention.

For example, the heatable regions may be in the form of a coating of the substrate having a thickness that is small compared to the extent within the first plane. However, it may also be that the heatable regions have a significantly greater thickness. However, even in this case, the relevant surface for the purposes disclosed herein is the one at which the emission of the infrared radiation is essentially generated and can be described by a normal in the direction of emission. Said surface forms the first plane. A normal to the first plane thus preferably indicates the emission direction in which the emitted intensity of the infrared radiation is strongest compared to other directions and/or which relates to the preferred direction of emission. Said first plane preferably simultaneously forms an (intersection) plane with the heatable and non-heatable regions.

The micro-heating element is preferably at least partially free-standing and allows, for example, thermal expansion within the IR emitter due to strong temperature changes as well as translational movements. Partially free-standing means that it is at least partially non-positively and/or positively connected to other elements of the emitter at the interfaces and therefore has a degree of freedom of movement in a direction essentially perpendicular to the interface.

Modulation of the intensity emitted by the infrared emitter (IR emitter) can be achieved by controlled and repeatable temporary blocking of the unmodulated beam by an element that is non-transmissive (opaque) for said beam. To this end, the aperture structure comprises transmissive (transparent) and non-transmissive (opaque) regions for infrared radiation. The aperture structure is preferably characterized in that it comprises transmissive and non-transmissive regions for infrared radiation within a plane parallel to the first plane of the heating element (second plane). The regions are preferably arranged within the second plane along a line.

The aperture (blend) structure is preferably a flat element which, with the exception of the regions transmissive (transmissive) to infrared radiation, consists of a material that is non-transmissive (opaque) to IR radiation. The transmissive regions can be formed, for example, by in-plane slots in the aperture structure. Similarly, in these regions a different material that is substantially transparent to the spectrum of radiation may be used. It may be equally preferred that the material (for forming the aperture) is substantially transparent to infrared radiation and the non-transmissive regions are formed, for example, by a coating substantially opaque to infrared radiation.

The non-transmissive regions of the aperture structure are of a material substantially opaque to infrared radiation. It is preferred that this material, when blocking infrared radiation therefrom, is not heated to such an extent that it itself begins to emit infrared radiation at a level that is contrary to the desired modulation characteristics. Thus, it may be desirable that the material substantially reflects the radiation and/or that any heat generated by absorption of the IR beam be sufficiently dissipated.

The arrangement or dimensioning of the transmissive and non-transmissive regions of the aperture structure is preferably matched to the arrangement or dimensioning of the heatable and non-heatable regions of the structured micro-heating element in such a way that, in the first position, the IR radiation emittable by the heatable regions is predominantly absorbed and/or reflected by the non-transmissive regions of the aperture structure, while in the second position the IR radiation emittable by the heatable regions predominantly radiates through the transmissive regions of the aperture structure. By suitable selection of the size as well as arrangement of the areas of the transmissive and non-transmissive regions of the aperture structure or of the heatable and non-heatable regions of the structured micro-heating element, it can thus be achieved, for example, that in a first position the IR radiation emittable from the heatable regions is almost completely absorbed by the non-transmissive regions of the aperture structure, while in a second position the IR radiation emittable from the heatable regions radiates almost completely through the transmissive regions of the aperture structure. By aligning the structuring of the micro-heating element and the aperture structure, a particularly high modulation depth or high extinction ratios can be thus achieved with simple means.

As an example the aperture structure may be essentially planar and rectangular and exhibit slit-shaped transmissive regions. These transmissive regions could run perpendicular to the long side of the rectangle, for example. Between the transmissive slits are essentially strip-shaped non-transmissive regions. It may be preferred that the transmissive regions are shorter than the transverse side of the rectangular aperture structure, so that all non-transmissive regions are connected to each other along at least one longitudinal side of the aperture structure. Even though in this case the non-transmissive regions geometrically form a connected surface, in the sense of the invention several non-heatable regions are present. In particular, transmissive and non-transmissive regions for IR radiation alternate along the center line of the cuboid, which allows for the modulation according to the invention with respect to a correspondingly structured heating element.

Preferably, a substantially free-standing, self-supporting aperture structure can be provided. In particular, the regions of the aperture structure that are transmissive (transparent) and non-transmissive (opaque) to infrared radiation are intended to transmit or block the unmodulated beam emitted by the micro-heating element depending on the positioning of the aperture structure within the second plane. Therefore, the aperture structure and micro-heating element shall be movable relative to each other such that the unmodulated beam is substantially blocked by the non-transmissive regions in at least a first (relative) position such that the intensity of the beam (on the side of the aperture structure facing away from the heating element) becomes minimal, and is substantially transmitted through the transmissive regions in at least a second (relative) position such that the intensity of the IR beam becomes maximal. Herein, the relative motion should take place between the two parallel planes. Preferably, the actual movement may be performed by the aperture structure in its plane and/or by the micro-heating element in its plane. The movement preferably takes place within one of the two planes along a preferred direction. The preferred direction can in particular be defined by the direction along which the regions of the micro-heating element and/or the aperture structure are arranged. When arranging the corresponding (non-)transmissive and (non-)heatable regions along a line, a linear relative movement is preferably intended. If the regions are arranged on a circle, a rotational movement may be preferred.

A person skilled in the art is familiar with the design and operation of various suitable actuators, in particular MEMS actuators for both linear translational and rotational movements, or can refer to the relevant technical literature (see, among others, Judy J. W. (2006) Microactuators. In: Korvink J. G., Paul O. (eds) MEMS: A Practical Guide to Design, Analysis, and Applications. Springer, Berlin, Heidelberg, E. Thielick, E. Obermeier Microactuators and their technologies Mechatronics Vol. 10, 4-5, 1 Jun. 2000, Pages 431-455, Elwenspoek, M., Wiegerink, R. J., Mechanical Microsensors, Springer, Berlin, Germany, 2001, M. Tabib-Azar Microactuators, Springer Science+Business Media New York 1998).

Terms such as substantially, approximately, about, etc. preferably describe a tolerance range of less than ±40%, preferably less than ±20%, particularly preferably less than ±10%, even more preferably less than ±5%, and especially less than ±1%. Similar preferably describes sizes that are approximately equal. Partially preferably describes at least 5%, more preferably at least 10%, and more preferably at least 20%, in some cases at least 40%. For example, if it is disclosed in the foregoing that a region is substantially transparent to an infrared beam, it is meant that the entire intensity of a beam or partial beam is transmitted through said region within the above tolerance ranges.

The aperture structure and the micro-heating element are movable in the parallel planes to each other. If the modulatable IR emitter is provided with a housing, the aperture structure and/or the micro-heating element is preferably movably mounted relative to said housing. Therefore, the movably mounted element may be connected to the rigid elements via a linear guide. A linear guide preferably allows linear movement along one direction and prevents movement or restricts the degree of freedom of movement in other directions. At the same time, a linear guide preferably allows movement along one direction with as little friction and maintenance as possible, for example by means of rolling elements and/or plain bearings.

The actuator is configured for a relative movement of the aperture structure and the micro-heating element. In particular, an actuator converts an electrical control signal into a movement. The actuator can be a MEMS actuator, which is for example an electrostatic actuator. The actuator can be directly connected to the movable aperture structure and/or the movable micro-heating element. In particular, it is preferred that the actuator is at the same time a connecting element (joint) of the movable element with the rigid part of the IR emitter, in particular the housing of the emitter. Thus, in particular, the actuator can furthermore be a linear guide at the same time. It is particularly preferred that the actuator is the only connecting link between the moving structure and the rest of the emitter. The moving structure can otherwise be essentially free-standing. In this way, a particularly simple and compact structure of the IR emitter may be achieved. It is particularly preferred that the micro-heating element is moved relative to the aperture structure by an actuator. Thus, by moving the heatable regions of the micro-heating element relative to the regions of the aperture structure that are transparent to IR radiation, a modulation of the IR beam can be performed by substantially blocking the IR radiation in at least one first position and transmitting it substantially completely through the transmissive regions in at least one second position, so that any intensity in the range between the minimum and maximum intensities reached in these two positions can be set in a desired time course. Thus, the first position preferably corresponds to a minimum intensity and the second position preferably corresponds to a maximum intensity.

The ratio between the maximum and minimum intensity of the emitted IR radiation, which can be adjusted by the relative movement, is referred to as an extinction ratio. The extinction ratio can be determined directly from the quotient between maximum intensity and minimum intensity, and preferably may be specified directly by said quotient. However, it may also be preferred that the ratio is expressed in the logarithmic scale decibel (dB), as is common in communications engineering, for example.

The actuator is preferably configured for the relative movement if it can perform the relative movement over the entire range at least between a first position and a second position at a modulation frequency suitable for a desired modulation frequency and can be driven by an electrical signal according to the requirements.

It may also be preferred that the aperture structure is moved relative to the heating element by an actuator. The modulation described above may be achieved in the same manner.

If the micro-heating element is characterized by several heatable regions, for example in strip form, the emitted beam of the IR emitter is characterized by the combined partial beams of the individual areas and their intensity. The exact geometric radiation behavior of the individual areas is thereby preferably dependent, i.a. on the overall design of the IR emitter, for example on the geometric design of the heatable regions, the distance from the aperture structure to the micro-heating element, the positioning of a lens for collimating the beam, etc.

For example, a lens can be placed between the heating element and the aperture structure, but it can also be placed on the side of the aperture structure facing away from the heating element. Moreover, a distance between the heating element and the aperture structure may be small enough such that the aperture structure is in the near field. Likewise, the distance may be greater so that the radiation at the aperture structure is described by the far field. Independent of this, it is preferred that in a first position within the relative motion between the aperture structure the beam is substantially blocked by the aperture structure and in another, second position the radiation or beam is substantially transmitted by the aperture structure. To achieve the desired extinction ratio during modulation, it is decisive that the ratio between the minimum and maximum intensity of the IR emitter is appropriate. Therefore, it may also be preferred that the beam is only partially transmitted even in the second position of maximum intensity as long as the beam is substantially blocked in the first position of minimum intensity, thus achieving a desired extinction ratio. Preferably, the intensity of the beam to be considered relates to the modulated intensity of the beam after it leaving the IR emitter and being available for further use. Preferably, the minimum and maximum intensities denote the spatially averaged intensities in the emission direction directly after the aperture structure.

It is preferred that the aperture structure is designed to the structure of the micro-heating element. In particular, this means that the regions transparent to IR radiation match the heatable regions of the heating element in shape, number and spacing, taking into account the divergence of the unmodulated radiation emitted by the heating element. In this manner, the desired modulation behavior may preferably be achieved individually for each partial beam emitted by a heatable region, and thus the total beam composed of the partial beams may equally be modulated as desired. For example, in the case of a micro-heating element comprising a plurality of parallel, strip-shaped heatable regions, it may also be preferred to use an equal number of parallel, strip-shaped transmissive regions of the aperture structure. A person skilled in the art would know how to design the IR emitter with respect to the aperture structure, the micro-heating element, the spacing of the two components, etc., to obtain the desired modulation characteristics. The person skilled in the art would know, for example, that he may have to select the non-transmissive strip-shaped regions of the aperture structure between transmissive strip-shaped regions wider than the heatable strip-shaped regions of the micro-heating element in order to account for the divergence of the emitted radiation and to block said radiation to a sufficient extent.

It is particularly preferred that an extinction ratio of at least 2 is achievable for the infrared radiation emitted by the micro-heating element through the aperture structure between the first and second positions. Said ratio is preferably the direct quotient between the maximum and minimum intensity. However, it may also be preferred to select the structuring to allow higher extinction ratios of, for example, at least 3, 4, 5, 6, 7, 8, 9, 10, 15, 20, 25, 30, 40, 50, 100, 200, 300, 400, 500 or 1000. The extinction ratio can likewise be expressed in dB, with extinction ratios of at least 3 dB, at least 10 dB, at least 20 dB, at least 30 dB, or at least 40 dB being preferred. The preferred extinction ratios allow for a particular well realization of the desired applications, e.g. in photoacoustic spectroscopy.

The maximum modulation frequencies achievable at the desired modulation depths should preferably be at least 1 kilo Hertz (kHz), particularly preferably at least 10 kHz, more preferably at least 20 kHz, particularly preferably at least 30 kHz, and especially at least 100 kHz. It is particularly preferred to achieve modulation frequencies in the range of audible sound and/or ultrasound for an application in photoacoustic spectroscopy. The modulation bandwidth over which the desired modulation depth is achieved preferably concerns the entire frequency range from 0 Hz to the maximum modulation frequency.

It may also be preferred that there are more positions than only a first and/or a second position where the intensity becomes minimum and/or maximum. It may be equally preferred that the positions relate only to local intensity maxima and/or minima, which however also fulfill the desired extinction ratio in conjunction with another position.

The desired modulation can preferably find expression in a corresponding temporal course of the emitted radiation intensity. To determine the feasibility of such a desired temporal intensity course, the modulation depth and the bandwidth over which this modulation depth is essentially achievable are of particular importance. Moreover, the resolution of an electronic control of the IR emitter is preferably relevant for feasibility. For example, it may be of importance which different intensity levels between minimum and maximum intensity can be achieved with which frequency. It is preferred that the IR emitter exhibits an electrical control that controls the micro-heating element and the relative movement between the heating element and the aperture structure.

Such a control can be realized e.g. by a control device. By means of a control device, the desired spectra, intensities and modulations may be set or adjusted. Control preferably means that electrical control signals are transmitted directly to the actuator and the micro-heating element, which result in the desired radiation properties. In the case of the micro-heating element, this means that in particular a specific temperature and/or a specific temporal temperature profile may be set or adjusted. Furthermore, a certain modulation signal can be obtained by the relative movement triggered by the actuator (possibly in coordination with a temperature course). Typically, the modulation signal is an analog signal generated by a control device. This in turn can preferably receive a suitable digital electronic signal, for example from a control computer, which is subsequently translated by the control device into suitable actuation signals.

It is particularly preferred a number of parts of the IR emitter, such as the micro-heating element and actuator are MEMS elements that exhibit small dimensions in the micrometer range and are produced according to standard manufacturing processes.

The structure of the modulatable infrared emitter will now be illustrated by means of a specific embodiment. The IR emitter is preferably accommodated in a housing consisting of a lower support, side parts and a cover element. Sealing elements can be provided between the carrier, the cover element and the side parts. The sealing elements may be used to reduce a thermal exchange of the micro-heating element housed inside the housing with the external environment of the housing. The cover element exhibit an applied aperture structure. The structured micro-heating element within the housing comprises individual, parallel heating lamellas whose surfaces oriented in the direction of the aperture structure represent heatable regions in a first plane. Along said first plane, non-heatable regions are located between the heatable regions. The regions are each arranged periodically. The aperture structure is arranged along a second plane parallel to the first plane and consists of regions that are transmissive (transparent) to infrared radiation and regions that are non-transmissive (opaque).

The relative movement is achieved by an actuator in the form of a comb drive, which is directly coupled to the micro-heating element. The actuator is in turn attached to a side part of the housing. The micro-heating element is only connected to the housing via the actuator and is otherwise free-standing.

In the exemplary embodiment described, the number of non-transmissive regions of the aperture structure is equal to the number of heatable regions of the micro-heating element. The regions are moreover arranged periodically. The width of the non-transmissive regions is slightly wider than that of the heatable regions, so that their IR radiation is substantially blocked when the heatable regions are positioned by means of the actuator directly below the non-transmissive regions in the first position in which the radiation emitted from the IR emitter exhibits a minimum intensity. By moving the heatable regions to a second position below the transmissive regions of the aperture structure, a maximum intensity of the emitted beam may be set. In this case, the regions are configured relative to each other such that an extinction ratio between the intensity of the radiation emitted in the second position and the intensity of the radiation emitted in the first position of at least 2 is achieved.

Such an IR emitter achieves a number of preferred characteristics, it is fast modulating, the modulation depth (extinction ratio) is suitable for many applications, it is compact, robust and durable. The bandwidth of the modulation is furthermore greatly improved compared to the modulation methods known from the prior art.

In a preferred embodiment of the modulatable infrared emitter, in the first position, IR radiation emittable from the heatable regions is predominantly absorbed and/or reflected by the non-transmissive (opaque) regions of the aperture structure, while in the second position, IR radiation emittable from the heatable regions predominantly traverses (passes through) the transmissive regions of the aperture structure.

The embodiment is a preferred embodiment of the modulatable infrared emitter due to a relative movement of the aperture structure and the micro-heating element between a first position and a second position. In this regard, the aperture structure and the micro-heating element are preferably geometrically aligned such that the heatable regions in the first plane and the non-transmissive regions in the second plane may be positioned on top of each other along a direction orthogonal to said planes.

Preferably, the non-transmissive regions completely cover the heatable regions and are positioned above the heatable regions in the direction of emission of the IR radiation. Completely covering means in particular that the non-transmissive regions have an extension in each direction within the second plane which is at least equal to, and particularly preferably greater than, the heatable regions in the first plane. It is preferred that each heatable region is assigned an opaque (non-transmissive) region in this way. However, a non-transmissive region can also be assigned to several heatable regions. Of importance is that the IR radiation emitted by the heatable regions is predominantly absorbed and/or reflected, i.e. above all is not transmitted, by the non-transmissive regions of the aperture structure.

It may be preferred that the non-transmissive regions substantially reflect, rather than absorb, the unmodulated radiation to avoid heating the aperture structure.

In a further preferred embodiment of the modulatable infrared emitter, the actuator is coupled to the heating element and configured for translational movement of the heating element relative to the aperture structure. In this embodiment, the aperture structure is preferably stationary, wherein a relative movement between the aperture structure and the micro-heating element results from a translational movement of the heating element, and the movement is initiated by the actuator. A translational movement refers in particular to a displacement of the heating element. The displacement is preferably to occur within the first plane. Coupled means in particular that there is a direct mechanical connection between the micro-heating element and the at least one movable element of the actuator, so that a movement of the movable actuator element triggers a movement of the heating element in the desired direction.

The actuator and heating element can preferably be directly connected to each other. It may even be preferred that both heating element and actuator comprise the same substrate and/or are made of the same substrate. There may be not only a mechanical, but also a thermal and/or electrical coupling to the actuator. Through thermal coupling, a desired non-radiative heat loss of the heating element can be achieved, which influences the radiative and/or modulation properties of the heating element in a desired manner. Electrical coupling may achieve electrical contacting of the heatable layer of conductive material of the heating element. Advantageously, if the heating element is movable, the aperture structure can be installed stationary, e.g. in a cover element of the housing, which increases the robustness of the emitter.

However, it may be equally preferred that the actuator is coupled to the aperture structure and configured for translational movement of the aperture structure relative to the heating element.

In the embodiment, the micro-heating element is preferably stationary, wherein the relative movement between the micro-heating element and the aperture structure is achieved by a translational movement of the aperture structure, and the movement is triggered by the actuator. A translational movement in this case preferably denotes a displacement of the aperture structure. This is preferably to occur within the second plane. In this embodiment, coupled means in particular that there is a direct mechanical connection between the aperture structure and the at least one movable element of the actuator, so that a movement of the movable actuator element triggers a movement of the heating element in the desired direction.

Actuator and aperture structure can preferably be directly connected to each other. It may even be preferred that both the aperture structure and the actuator comprise the same substrate and/or are made of the same substrate. There may be not only a mechanical but also a thermal coupling between the actuator and the aperture structure. The thermal coupling can be used to dissipate heating of the aperture structure by any absorbed radiation. However, it may also be desirable that the aperture structure and the actuator are thermally decoupled to prevent a heat transfer from the heating element to the structure via the actuator.

In a further preferred embodiment of the modulatable infrared emitter, the infrared emitter comprises a housing in which the aperture structure, the micro-heating element and the actuator are present installed. Here, it is particularly preferred that the aperture structure is thermally decoupled from the housing.

Preferably, the housing may be based on the dimensions and shapes of the installed components, it may be equally preferred that the housing is significantly larger than the installed elements to improve handling of the emitter and create a robust device. For example, the micro-heating element, actuator and/or aperture structure may be MEMS elements and/or have dimensions in the (sub-) micron range, with the housing having dimensions in the centimeter range.

It is possible, as already described above, that the actuator within the housing is directly coupled to the micro-heating element/aperture structure. Moreover, a general structure of the emitter, comprising a housing has already been described in an exemplary embodiment above.

Preferably, the housing exhibits a continuous outer surface and is closed on the inside. The micro-heating element is installed inside the housing. This allows it to be protected from external influences and prevents emission of IR radiation to the outside except through the transmissive regions of the aperture structure in appropriate positioning. The actuator can preferably be attached to a side part of the housing.

It is preferred that the micro-heating element is not thermally isolated from the housing, but rather that non-radiative heat dissipation from the heating element to the housing is possible so that heat can dissipate from the heating element. For example, a desired balance can be established between the heat generated by the current-carrying, heatable layer of conductive material and the heat dissipated from the heating element to the environment, the desired radiation characteristics can be produced, and/or the desired modulation characteristics can be achieved.

It may be preferred, for example, that the components housing, micro-heating element and/or actuator are made of the same material and that there is sufficient thermal conduction between directly connected elements.

The housing may preferably comprise a heat sink for its own heat dissipation.

It is desirable that the aperture structure, which is also present installed in the housing, is thermally decoupled from the other elements, in particular from the housing. This preferably means that by using at least one suitable material at the connection between the aperture structure and the housing or actuator and/or by a suitable design of the connection point (for example small connection area and/or suitable thickness of the connection) the aperture structure does not heat up significantly. Heating up is preferably described in relation to a temperature of the aperture structure when the micro-heating element is switched off and in thermal equilibrium.

Likewise, it may be preferred that the time constant essential for determining the time course of the approximation of the temperature of the aperture structure to the housing is sufficiently large. This can, for example, be greater than 1 minute, preferably greater than 10 minutes, and in particular greater than one hour.

A suitable material at the joint preferably covers the entire joint surface. Suitable materials refer in particular to the thermal conductivity of the materials, expressed in watts per meter and kelvin (W/m·K). Preferred thermal conductivities at the junction are less than 10 W/m·K, particularly preferably less than 1 W/m·K and especially less than 0.1 W/m·K.

Preferably, an oxide layer is introduced at the connection point between the aperture structure and the housing or actuator and/or between the actuator connected to the aperture structure and the housing to provide the desired thermal decoupling. An oxide layer is particularly well suited to providing thermal decoupling in the materials used for the aperture structure. Moreover, they are particularly easy and inexpensive to produce.

In order to minimize the direct transfer of heat between the micro-heating element and the aperture structure, it may be preferred that the housing is configured for generation of a vacuum in a space between these components or between the first and second planes. A vacuum preferably refers to a pressure of less than $30 \times 10^3$ Pascals (Pa), more preferably less than 100 Pa, and more preferably 0.1 Pa or less. Configured means that the housing is designed to be sufficiently pressure tight. It is also preferred that the housing comprises a connection for a vacuum pump or an integrated vacuum pump. However, it is equally preferred that the housing is substantially permanently evacuated during manufacture.

It may also be preferred that the aperture structure is cooled to minimize its own emission of unmodulated IR radiation in the direction of the modulated beam. For example, Peltier elements and/or fluid cooling may be used to this end.

In a further preferred embodiment of the modulatable infrared emitter, the housing comprises a cover element in which the aperture structure is presently fixated and in which at least one optical filter is additionally installed in the cover element. The aperture structure is thus preferably integrated into the housing and is present on one outer surface of the housing, which is formed by the cover element. The aperture structure may essentially form the cover element or be comprised by the cover element.

Depending on the use of the IR emitter, e.g. in various spectroscopy methods, either the entire broad frequency spectrum of the thermal radiation source may be used or narrower spectra are desired. To select a desired spectrum, which differs significantly from the unmodulated spectrum of the micro-heating element, frequency filters can preferably be employed. Advantageously, these may be integrated into the cover element.

Filters may be positioned between the micro heater and the aperture structure as well as on the other side of the aperture structure.

The filters used can advantageously exhibit different filter characteristics, e.g. band-pass filters, short-pass filters, long-pass filters, notch filters and any combination of these filters that lead to the desired spectral influences may be used. The frequencies or frequency ranges in which the filters act can be chosen flexibly depending on the application.

For example, a filter wheel can be used as a filter, on which filters with different filter properties are installed. The desired filter can be selected mechanically by rotating the filter wheel. Preferably, the filter wheel can be rotated by an electric drive.

The use of a Fabry-Perot filter is also conceivable. Such a filter can be used, for example, to select very narrow spectra. Preferably, the Fabry-Perot interferometer on which the filter is based tunable, for example by tuning the temperature or by mechanical adjustment. Thus, desired spectra can be flexibly selected from the original beam.

Likewise, suitable thin-film filters can preferably be used. These are particularly easy to manufacture and are very compact. In particular, if the IR emitter is manufactured in an integrated design in a manufacturing process, the production of such a thin-film filter can be easily integrated into the process. This reduces costs.

A flexible combination of thin-film filters or employment of a thin-film filter tunable for example by changing the temperature is also advantageous.

Filters for other properties of the IR radiation, e.g. polarization, can also be used. Preferably they may also be part of the cover element.

In a preferred embodiment of the modulatable infrared emitter, the micro-heating element comprises a substrate on which is deposited, at least in part, a heatable layer of a conductive material on which contacts for a current and/or voltage source are present.

The substrate preferably forms the base of the micro-heating element. In this context, the substrate may also comprise other components of the IR emitter, such as the actuator and/or housing elements, at least in part. Advantageously, the substrate can be suitably formed by established process steps, in particular from semiconductor and/or microsystem manufacturing. Subsequently, preferably, a heatable layer of a conductive material can be applied to or integrated into the substrate, e.g., by doping and/or coating. The heatable layer preferably comprises the heatable regions of the micro-heating element. It is preferred that the heatable layer is contacted to a source of electrical energy to establish electrical contact. Primarily, the contacting is to be performed such that the heatable regions are at least partially traversed by electric current and emit IR radiation in a desired manner.

In a further preferred embodiment of the modulatable infrared emitter, the substrate is selected from a group comprising silicon, monocrystalline silicon, polysilicon, silicon dioxide, silicon carbide, silicon germanium, silicon nitride, nitride, germanium, carbon, gallium arsenide, gallium nitride and/or indium phosphide. These materials are particularly easy and inexpensive to process in semiconductor and/or microsystem manufacturing and are also well suited for mass production. Likewise, these materials are particularly suitable for doping and/or coating in order to achieve the desired electrical, thermal and/or radiation properties in certain regions.

In a further preferred embodiment of the modulatable infrared emitter, the conductive material for forming the heatable layer is selected from the group comprising platinum, tungsten, (doped) tin oxide, monocrystalline silicon, polysilicon, molybdenum, titanium, tantalum, titanium-tungsten alloy, metal silicide, aluminum, graphite and/or copper. On the one hand, these materials exhibit the desired thermal, electrical, mechanical and/or radiation properties, and on the other hand, they are particularly easy and inexpensive to process.

In a further preferred embodiment of the modulatable infrared emitter, the micro-heating element comprises a lamellar structure, a meander structure, and/or a grid structure.

A lamellar structure preferably refers to an arrangement of similar layers running in parallel. The heatable layers of conductive material are preferably arranged in lamellar form. The individual layers, also referred to as lamellae in the following, are preferably arranged with their surface perpendicular to the first plane.

It may be preferred that the lamellae are planar, which means in particular that their extension in each of the two dimensions of a surface is greater than in a dimension of the thickness perpendicular thereto. For example, the size ratios can be at least 1.5 to 1. Significantly larger ratios of, for example, 5 to 1 or 10 to 1 are also covered herein. The intersecting surfaces of the lamellae with the first plane, or the side surfaces of the lamellae lying in the first plane, preferably form the heatable regions of the micro-heating element.

It is preferred that between the lamellae regions are present, which may be parts of the substrate which do not comprise heatable layers of conductive material. The intersection of these regions with the first plane preferably form the non-heatable regions. The regions between the lamellae are preferably adapted for thermal expansion of the lamellae.

It is preferred that the heatable lamellas are electrically contacted to each other via the substrate situated between them, thus exhibiting a common contact to an electrical energy source.

Lamellae are particularly easy and inexpensive to produce on a substrate and are especially well suited for use as heatable regions.

A meander structure preferably denotes a structure comprising a sequence of mutually orthogonal sections. Such a meander structure can, for example, be formed from the above lamellar structure if adjacent lamellas are connected to one another at a side face. The meander structure is preferably formed by a heatable layer of conductive material.

A meander structure can be arranged in different ways within the IR emitter. Preferably, the first plane or a plane parallel to it can be used as a defining plane of the structure, e.g. as a symmetry plane. The intersecting surfaces and/or boundary surfaces of the meander structure with the first plane preferably form the heatable regions. It is preferred to arrange the meander structure in such a way that the area of the heatable regions is maximized.

Preferably, between substantially adjacent parallel connected orthogonal sections of the meander structure a substrate is present situated that does not include a heatable layer of conductive material.

Such a meander structure can convey advantages during manufacture. In particular, such a structure inherently provides electrical contact for all heatable layers of conductive material or all heatable regions.

A meander structure, by virtue of being a continuous heatable layer of conductive material, can exhibit a high resistivity and thus be particularly efficient in producing a temperature distribution desired for IR radiation.

A grid (or mesh, lattice, grating) primarily refers to a periodically arranged structure. This structure is preferably formed by at least one heatable layer of conductive material. Preferably, the structure has interfaces and/or intersections with the first plane representing the heatable regions of the micro-heating element. Preferably, the periodic structure is disposed along the first plane and maximizes the area of the heatable regions. Preferably, non-heatable regions are located between adjacent heatable regions.

Such a grid provides great flexibility for the structuring of the micro-heating element.

In a further preferred embodiment of the modulatable infrared emitter, with respect to the possible relative movement between the micro-heating element and the aperture structure, in the first plane the heatable and non-heatable regions of the micro-heating element and in the second plane the transmissive and non-transmissive regions of the aperture structure are periodically arranged.

The periodicity preferably denotes a repeating spatial distance of the regions within the first or second plane. The distance is preferably measured for the regions between two equally arranged points within adjacent regions. An example of such a periodic arrangement are strip-shaped heatable and/or transmissive regions which have the same distance from each other in the transverse direction. It is further preferred that the respective strips have the same dimensions. However, the latter is not necessary for the periodicity of the strips. Strips of different widths may also exhibit periodicity, which becomes apparent, for example, when the distance between adjacent regions is measured between the perpendicular bisector of the transverse sides. The non-heatable regions and/or non-transmissive regions, which are situated between the complementary, heatable regions and the transmissive regions, respectively, and are also essentially strip-shaped, typically likewise exhibit a periodicity due to the periodicity of the complementary areas, which can be determined between at least two points of these regions.

By providing a periodic structure, a desired beam and/or modulation behavior can be achieved in a particularly simple manner. For illustration imagine a single strip-shaped, heatable region. In this case, the aperture structure comprises two strip-shaped, transmissive regions, between which there is a non-transmissive (opaque) strip-shaped region. Now, the micro-heating element is to be translated back and forth at a predetermined frequency f for modulation. Here, a translation period includes the following movement: from the position of the heatable region under the non-transmissive region to a position under one transmissive region then to the other transmissive region and back to the starting point. Thus, within one translational movement, two positions are reached where the transmission becomes maximum (second position) and twice the same first position where the transmission becomes minimum.

Thus, in this example, the IR emitter may achieve an approximate averaged modulation frequency of the IR beam of 2·f at a translation frequency of f. In calculating the modulation frequency, it is preferable to note that the translational motion at and near the reversal points of the reciprocating motion has a different velocity than in the middle between two reversal points. Thus, the modulation frequency is typically only approximately a multiple of the translation frequency.

A variety of combinations of periodically arranged, (non-) heatable regions and/or (non-) transmissive regions are conceivable in order to produce a wide range of desired modulation and/or beam properties. For example, constellations may be selected in which a modulation frequency of approximately x·f can be achieved, where f is the frequency of the translational motion and x is an integer, preferably determined by the number of second and first positions passed.

The above-mentioned, lamellar, meander and/or grid structures are particularly suitable for periodically structured micro-heating elements.

In a further preferred embodiment of the modulatable infrared emitter, the spatial period of the arrangement of the heatable and non-heatable regions of the micro-heating element is equal to the spatial period of the arrangement of the transmissive and non-transmissive regions.

By matching the periods of both regions in such a manner, further advantages may be achieved. For example, it may be preferred that a plurality of periodically arranged heatable regions are used to generate the modulated beam to obtain a desired intensity and/or beam profile. If periodically equally arranged (non-) transmissive regions of the aperture structure are used for this purpose, modulation with a desired extinction ratio and frequency can be achieved even with very small translational movements. As a consequence, a very efficient and miniaturized IR emitter with a large modulation bandwidth may be provided. In particular, smaller translational motions can often be performed at higher speed and/or frequency and/or by using MEMS actuators.

Preferably, the number of heatable regions is equal to the number of non-transmissive regions.

Furthermore, it is preferred that the translational motion is performed such that the same number of heatable regions is always below a transmissive region in every second position so that the intensity is unchanged between different second positions.

It may also be preferred that there are more heatable regions than transmissive regions, or more transmissive regions than heatable regions. Thus, preferably, for a translational frequency of f, a smaller deviation of the actual frequency from the approximate average modulation frequency x·f can be obtained, since a plurality of second positions at which the intensity is maximum can preferably be passed at substantially the same rate.

In a preferred embodiment of the modulatable infrared emitter, the actuator is a MEMS actuator, preferably selected from the group comprising electrostatic actuator, piezoelectric actuator, electromagnetic actuator, and/or thermal actuator.

A MEMS actuator is preferably an actuator that is manufactured using standard microsystems technology manufacturing methods and also advantageously exhibits dimensions in the order of μm. Such an actuator is particularly compact, robust and low-maintenance and can be manufactured easily and inexpensively. In particular, a number of parts of the emitter can be MEMS elements, i.e., elements with the preferred properties mentioned above, and can be manufacturable in one manufacturing step with the MEMS actuator. Desirably, the same substrate can be used in parts for fabrication. This simplifies and cheapens the manufacturing process.

The above actuators are particularly well suited for a large number of fast, periodic translational movements and have low energy requirements, especially due to their compact design. The range of achievable translation speeds is moreover high due to the compact design, low inertias and linear motion.

For modulation purposes, it may be desirable to dissipate heat from the micro-heating element to the largest possible extent preferably through the coupled actuator to the housing. Therefore, it may be preferred that the actuator is substantially or partially made of the housing material.

In further preferred embodiment of the modulatable infrared emitter, the MEMS actuator is an electrostatic actuator in the form of a comb drive based on a variation in comb overlap and/or comb spacing.

MEMS comb drives are known from the prior art, e.g. from patent application DE 10 2017 206 183 A1. Depending on the embodiment, the comb overlap and/or the comb spacing can be varied.

It has been recognized that such MEMS comb drives due to their dimensions and generatable movements are particularly suitable for a preferential translational motion and compact IR emitter.

In a further preferred embodiment of the modulatable infrared emitter, the non-transmissive regions of the aperture structure have a transmittance of less than 0.1 in a wavelength range within 780 nm to 1 mm and the transmissive regions of the aperture structure have a transmittance of greater than 0.9.

Preferably, the transmittance describes the portion of the intensity of the IR radiation generated by the micro-heating element incident on the respective region that completely traverses (penetrates) the region. The transmittance depends on the spectrum of the incident radiation, the material used and the thickness of the material to be traversed. A person skilled in the art knows how to achieve the desired properties. It is particularly preferred that the non-transmissive (opaque) regions have a transmittance of less than 0.05, more preferably 0.01 and especially less than 0.005.

The transmissive regions preferably have a transmittance of more than 0.95 and especially of 0.99.

As described above, it is preferred that the non-transmissive regions are essentially reflective and only weakly absorptive so that the aperture structure does not heat up excessively and emit IR radiation itself.

The aperture structure preferably comprises metals, in particular metals selected from the group comprising aluminum (Al), copper (Cu), gold (Au), silver (Ag), dielectric material such as $Al(MgF_2)$ and/or alternating layers. In particular, these materials can be used either as solid material (plate) with a thickness of preferably >1 μm and/or as coating of a thickness of typically 100 nm-1 μm. Particularly preferably, the aforementioned materials and/or layer thicknesses can create non-transmissive regions in the aperture structure which prevent unwanted IR emission with high efficiency.

With an aperture structure designed in this manner, the preferred emission and modulation characteristics of the emitter with a desired extinction ratio can be achieved in conjunction with a geometric matching between the regions of the aperture structure and the regions of the micro-heating element.

In another aspect, the invention relates to a manufacturing method for an infrared emitter as described above, wherein the manufacturing of the micro-heating element comprises the following steps:
  etching of the substrate;
  deposition of a conductive material on the substrate;
  optionally, patterning (structuring) the conductive material to form a heatable layer;
  contacting the conductive material.

For example, one of the preferred materials mentioned above can be used as the substrate. During etching, a blank, for example a wafer, can be formed into the desired basic shape of the micro-heating element. In a next step, the conductive material for the heatable layer is deposited. In particular, the heatable regions are to be included.

If further structuring (patterning) of the conductive material is desired, this can be carried out, for example, by further etching processes. Likewise, additional material can be deposited or doping can be carried out by usual processes.

For contacting the conductive material, suitable material such as copper, gold and/or platinum can additionally be deposited on the conductive material by common processes. Physical vapor deposition (PVD), chemical vapor deposition (CVD) or electrochemical deposition can preferably be used to this end.

In this way, a particularly finely structured micro-heating element can be produced, which preferably has dimensions in the micrometer range. Likewise, these manufacturing steps have proven particularly successful and belong to standard process steps in semiconductor processing.

In a further preferred embodiment of the manufacturing process, etching and/or patterning (structuring) is selected from the group comprising dry etching, wet chemical etching and/or plasma etching, in particular reactive ion etching, reactive ion deep etching (Bosch process); and/or deposition selected from the group comprising physical vapor deposition (PVD), in particular thermal evaporation, laser beam evaporation, arc evaporation, molecular beam epitaxy, sputtering, chemical vapor deposition (CVD) and/or atomic layer deposition (ALD).

These processes are particularly suitable for the fabrication of fine structures with sizes in the micrometer range. In particular, the Bosch process can produce very fine structures with a high aspect ratio, which are advantageous for a compact, efficient micro-heating element that is preferably fully integrated into the rest of the emitter structure.

In another aspect, the invention relates to a system comprising
a) a modulatable infrared emitter described herein
b) a control device,
wherein the control device is configured to regulate the actuator for relative movement of the heating element and the aperture structure between a first position and a second position.

The control device preferably enables an input and converts this input into suitable control signals. For example, an input may be a desired spectrum, intensity, and/or modulation frequency. The control device primarily generates appropriate analog electrical signals, which are passed to the actuator and/or the micro-heating element to generate the desired IR radiation.

However, more complex signals can also serve as input, which specify an exact temporal amplitude curve of the outgoing IR radiation for a desired spectrum. The control device in this case also preferably provides suitable control signals for generating the desired modulated IR radiation.

In particular, the control device is configured for a regulation of the actuator for the relative movement between heating element and aperture structure between (at least) a first and (at least) a second position. For this purpose, electrical signals are generated which trigger the required translational movement of the actuator.

Preferably, the control device comprises a control loop, wherein a feedback mechanism can be used to correct a discrepancy between desired control and actual movement of the actuator and/or heating of the micro-heating element.

It may be preferred that also the temperature profile of the micro-heating element for additional slow modulation of the IR radiation can be regulated by the control device.

The control device of the system can be positioned externally or integrated into the IR emitter.

The control device preferably comprises a processor, for example a microprocessor. Other integrated circuits used in digital electronics for control may likewise be used.

The use of such a system include a suitable control device can considerably simplify the desired use of the IR emitter.

For example, suitable spectroscopy signals can be designed on a PC. Via the input, the desired signals are subsequently transmitted to the control device. The control device in turn generates the drive signals, which produces a corresponding IR signal in high agreement with the theoretical specifications.

A control device, in particular in the form of a controller integrated in the emitter, is very compact and easy to handle. The control device preferably comprises a suitable interface for connection to a computer, for example. It may also be desirable that data can be transferred from the controller to the input device via this interface, such as the current temperature of the heating element or other status information.

In a further preferred embodiment of the system, the control device is configured to regulate the temperature of the heatable regions of the micro-heating element, preferably in a range between 50° C. and 1000° C.

Such a control device is preferably capable of providing suitable electrical power to the micro-heating element. In particular, it should be possible to adjust the temperature sufficiently precisely and/or to keep the temperature constant. A control mechanism with a feedback loop can be used to this end. To measure the current temperature of the micro-heating element, for example, at least one temperature sensor can be integrated at a suitable location on the heating element.

Such a control device allows the spectrum and/or the intensity of the IR emitter to be controlled particularly easily and reliably.

In a further preferred embodiment of the system, the control device is configured to regulate the actuator for oscillatory relative movement of the heating element and the aperture structure, passing (traversing) at least a first and second position during a period of the oscillation.

Preferably, the translational movement triggered by the actuator is repeated regularly between (at least) a first and (at least) a second position, so that an oscillation occurs between the positions and the translational movement exhibits a periodicity. Thereby, at the end of the translational movement, the starting point of the movement shall preferably to be reached again and the movement is to be executed anew in the following period. At a translation frequency of f, as mentioned above, the number of passes (traverses) x of a first and a second position indicates the resulting modulation frequency by x·f. Preferably, the same first and/or second positions can be passed several times as well as several first and/or second positions can be passed one translation period.

It is also possible to make a stepless adjustment of the translation frequency and thus the modulation frequency within the scope of the electronic resolution and/or bandwidth of the control device and/or the actuator. Thus, the modulation frequency can preferably be varied over time.

It may be further preferred that not only the translation frequency but also the translation amplitude is varied within the range of motion possibilities of the actuator. For example, depending on the design of the aperture structure and/or the heating element, the number of different first and/or second positions passed (traversed) within one translation period can be varied. Thus, for example, as described above, the modulation frequency of the IR radiation can also be varied while the translation frequency remains constant.

Thereby a system is provided through which a very flexible and efficient variation of the modulation frequency of the IR radiation can be achieved.

In a further preferred embodiment of the system, the control device is configured to regulate the actuator for an oscillatory relative movement of the heating element and the aperture structure such that a modulation frequency of the radiant power of the emitted infrared radiation is achieved between 10 Hz and 100 kHz, particularly preferably between 100 Hz and 20 kHz.

To this end it is particularly preferred that all required components, such as control equipment, actuator, etc., enable the required bandwidth.

The above frequencies have proven to be particularly effective for the preferred applications in the field of spectroscopy. In particular, these frequencies have proven to be especially suitable for use in photoacoustic spectroscopy, as they cover a wide range of acoustic frequencies, the generation of which is the primary focus of this spectroscopy method.

In another aspect, the invention relates to a method for modulated emission of infrared radiation comprising.
providing a modulatable infrared emitter according to any of the described embodiments;
heating the heatable regions of the micro-heating element to emit an infrared radiation;
controlling the actuator for relative movement of the aperture structure and the micro-heating element between at least a first position and a second position to modulate the radiant power of the emitted infrared radiation.

The average person skilled in the art will recognize that technical features, definitions and advantages of preferred embodiments of the IR emitter and system according to the invention also apply to the method according to the invention.

In another aspect, the invention relates to the use of a modulatable infrared emitter according to the preceding description or a system according to the preceding description for a spectroscopy method selected from the group comprising photoacoustic spectroscopy and/or infrared spectroscopy.

The described IR emitter may especially be used in infrared spectroscopy. However, a compact, long-life IR emitter that has a broad spectrum and can be modulated is of interest for a variety of applications.

For example, time-resolved measurements can be used to select specific frequency ranges of the IR emitter by using a tunable filter to select different frequencies of the spectrum of the emitter at different times. Modulation can in turn block certain frequencies from this and transmit others, so that IR pulses with essentially well-defined frequencies are emitted. As a result, in a time-resolved recording, e.g. of an absorption spectrum, the frequency absorbed in each case can be determined precisely.

The use of a compact, long-life and high-frequency modulatable IR emitter in photoacoustic spectroscopy is particular advantageous. Especially for photoacoustic spectroscopy, many applications are conceivable that do not take place in the laboratory and must function in everyday life. Examples are military applications for the detection of poisonous gas or the detection of (harmful) substances in the ambient air. Due to the high modulation frequencies, better signal-to-noise ratios can be achieved compared to direct modulation of the heating element, and a non-direct modulated emitter is also more durable.

In another aspect, the invention relates to a photoacoustic spectroscope for analyzing gas, comprising.
a modulatable infrared emitter according to any of the foregoing described embodiments, an analysis volume fillable with gas,
an acoustic detector, wherein the analysis volume is positioned between the infrared emitter and the acoustic detector so that the infrared radiation modulatably emitted by the infrared emitter can be used for photoacoustic spectroscopy of the gas.

The person skilled in the art is familiar with photoacoustic spectroscopy, how the technique is carried out and which components are used in the process. Due to the compact and long-life IR emitter, which is not known from the prior art, the whole setup can be manufactured in a particularly compact way suitable for everyday use. Due to the high modulation frequencies, the analysis possibilities are extremely versatile. At the same time, the signal-to-noise ratio can be increased, which is better for an acoustic detector with higher frequencies. A typical 1/f noise can thus be reduced, for example.

DETAILED DESCRIPTION

In the following, the invention will be explained in more detail by means of examples and figures, without being limited to them.

SHORT DESCRIPTION OF THE IMAGES

DETAILED DESCRIPTION OF THE IMAGE

Figure 1:
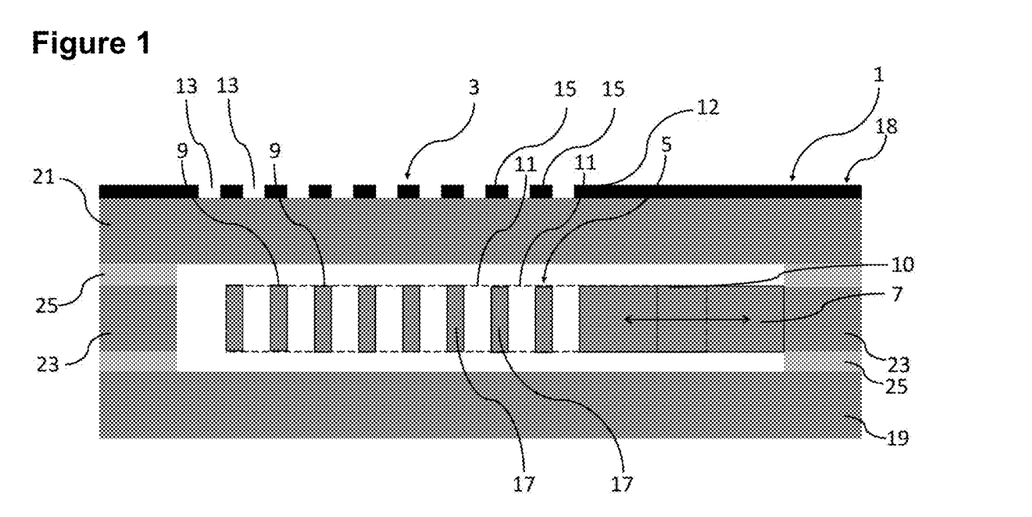
FIG. 1 shows a schematic diagram of the IR emitter.

FIG. 1 shows a schematic cross-sectional view of the modulatable infrared emitter 1. The IR emitter is accommodated in a housing 18, which consists of a lower support 19, side parts 23 and a cover element 21. Sealing elements 25 may be present between the support 19, cover element 21 and side parts 23, respectively. These sealing elements 21 are used to reduce thermal exchange of the interior of the emitter 1, in which the micro-heating element 5 is present, with the external environment of the IR emitter 1. The cover element 21 comprises an applied aperture structure 3 at the top. The structured micro-heating element 5 within the housing 18 comprises individual, parallel heating lamellae 17. The surfaces of the heating lamellae 17 oriented in the direction of the aperture structure 3 represent heatable regions 9 in a first plane 10. Along said first plane 10, periodically arranged non-heatable regions 11 are located between the periodically arranged heatable regions 9. The aperture structure is arranged along a second plane 12, which is parallel to the first plane 10 and consists of regions 13 which are transmissive (transparent) to infrared radiation and regions 15 which are non-transmissive (opaque). These are also arranged periodically and have the same period. The relative movement between the heating element 5 and the aperture structure 3 is realized by an actuator 7 in the form of a comb drive, which is directly coupled to the micro-heating element 5. The actuator 7 is in turn attached to a side part 23 of the housing 18. The micro-heating element 5 is free-standing except for the connection to the actuator 7.

The number of non-transmissive regions 15 of the aperture structure 3 is equal to the number of heatable regions 9 of the micro-heating element 5. The width of the non-transmissive regions 15 is slightly wider than that of the heatable regions 9 so that their IR radiation is substantially blocked when the heatable regions 9 are positioned in a first position directly below the non-transmissive regions 15 by means of the actuator 7. In said first position, the radiation emitted from the IR emitter 1 exhibits a minimum intensity. By moving the heatable regions 9 to a second position (not shown) below the transmissive regions 13 of the aperture structure 3, a maximum intensity of the emitted beam can be set. In this case, the regions are designed in such a way that an extinction ratio between the intensity of the radiation emitted in the first position and the intensity of the radiation emitted in the second position of at least 2 is achieved.

Figure 2:
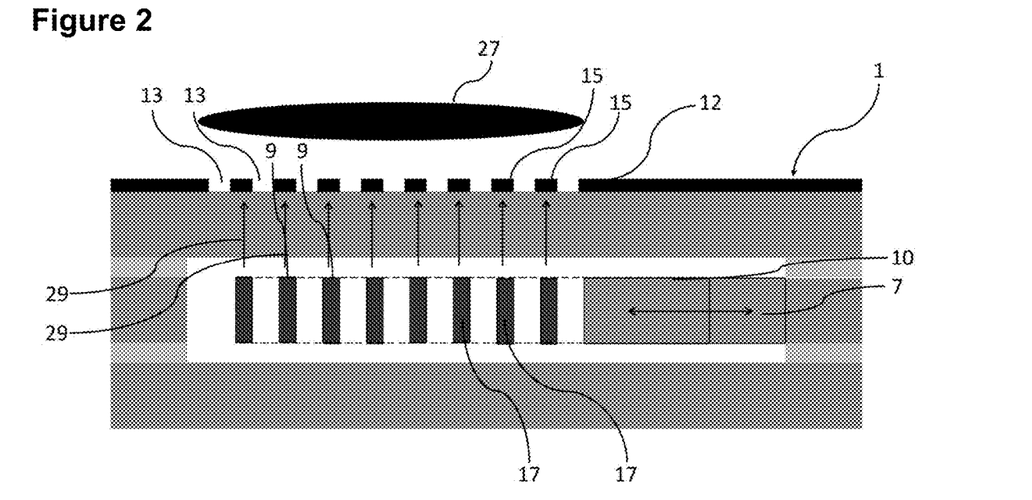
FIG. 2 shows a schematic representation of the IR emitter during a translation period of the heating element to modulate the IR beam at time T=0.

FIG. 2 shows the modulatable infrared emitter 1 of FIG. 1 during a translation period, at time T=0, at the beginning of the period. Here, all heatable regions 9 of the micro-heating element 5, which is directly coupled to the actuator 7, are positioned by the latter in a first position directly below the non-transmissive (opaque) regions 15 of the aperture structure 3. In this case, the unmodulated radiation 29 emitted by the heatable regions 9 is substantially absorbed and/or reflected by the non-transmissive regions 15 and the emitted intensity of the IR beam is minimal. In the embodiment shown, a lens 27 is present on the emitter above the aperture structure 3 and used to collimate the modulated infrared beam.

Figure 3:
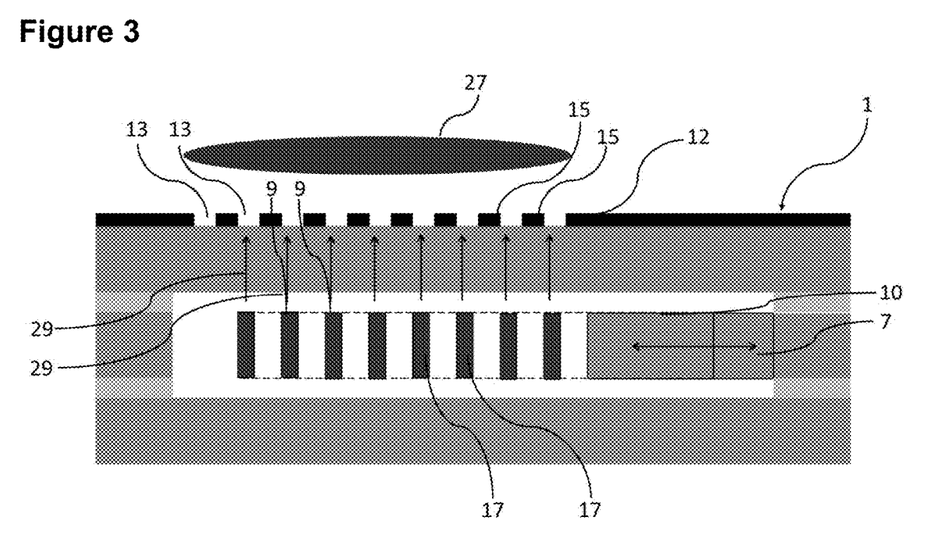
FIG. 3 shows a schematic representation of the IR emitter during a translation period of the heating element to modulate the IR beam at time T=¼.

FIG. 3 shows the modulatable infrared emitter 1 during the translation period at time T=¼, after one quarter of the period length. Here, all heatable regions 9 of the micro-heating element 5 are positioned by the actuator 7 in a second position directly below the transmissive regions 13 of the aperture structure 3. The translational movement of the micro-heating element 5 by the actuator 7 proceeds to the right. Thereby, the unmodulated radiation 29 essentially radiates through the transmissive regions 13 and the emitted intensity of the IR beam is maximal.

Figure 4:
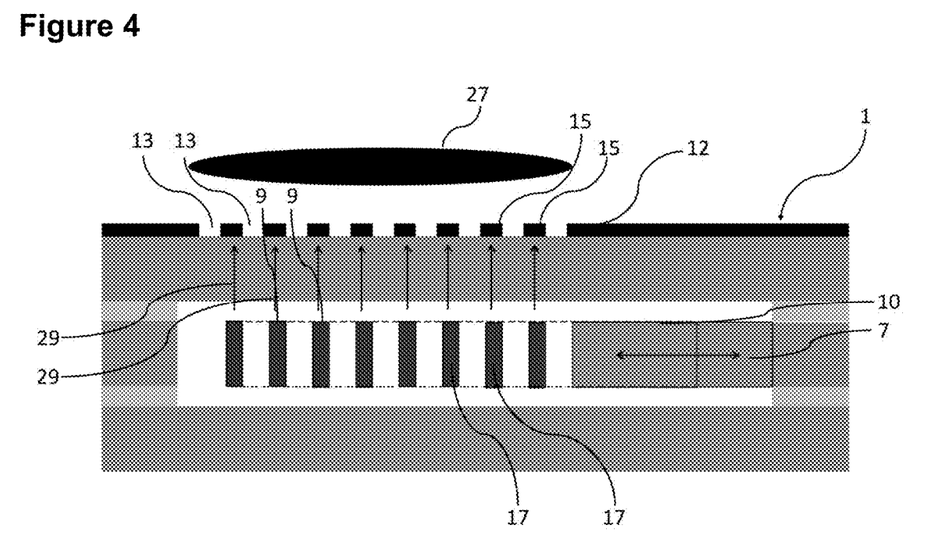
FIG. 4 shows a schematic representation of the IR emitter during a translation period of the heating element to modulate the IR beam at time T=2/4.

FIG. 4 is a representation of the modulatable infrared emitter 1 during the translation period at time T=2/4, after half of the full period duration. The micro-heating element 5 has been translated back to the initial position to the left. As at time T=0 in FIG. 2, all heatable regions 9 of the micro-heating element 5 are positioned by the actuator 7 in the (same) first position directly below the non-transmissive regions 15 of the aperture structure 3 and the unmodulated radiation 29 is substantially absorbed and/or reflected. The emitted intensity of the IR beam is again minimal.

Figure 5:
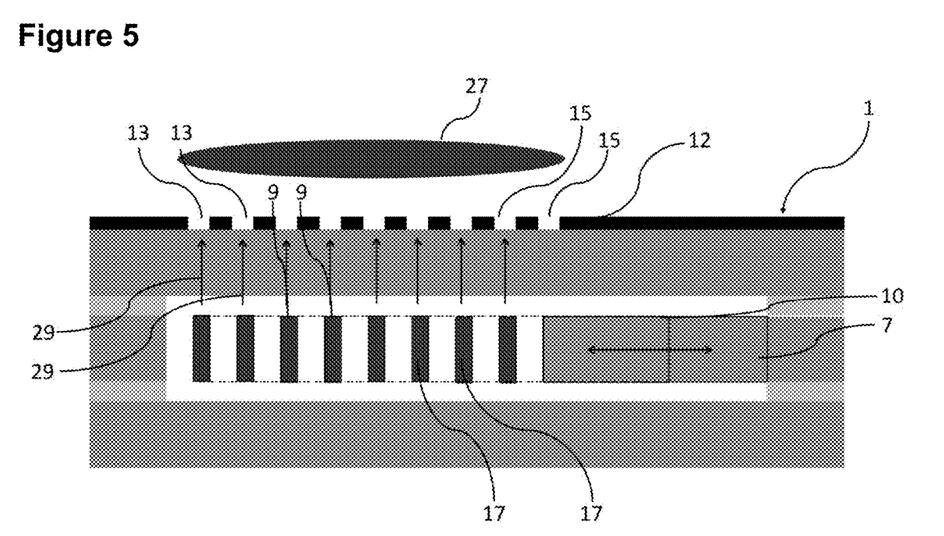
FIG. 5 shows a schematic representation of the IR emitter during a translation period of the heating element to modulate the IR beam at time T=¾.

FIG. 5 shows the modulatable infrared emitter 1 during the translation period at time T=¾, after three quarters of the period length has passed. The heatable regions 9 of the micro-heating element 5 have been translated further to the left by the actuator 7 to another second position directly below the transmissive regions 13 of the aperture structure 3. The unmodulated radiation 29 now again radiates essentially through the transmissive regions 13, and the emitted intensity of the IR beam is again at a maximum.

Figure 6:
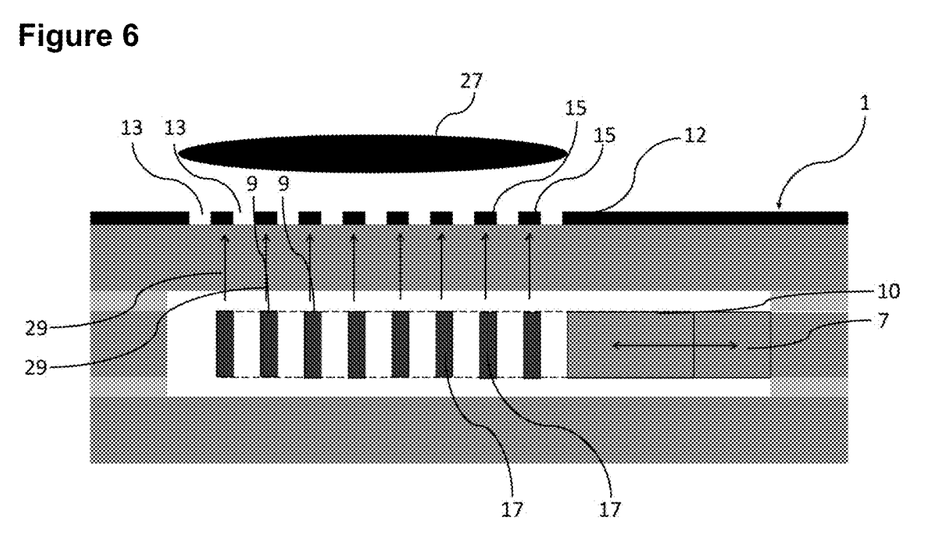
FIG. 6 shows a schematic representation of the IR emitter during a translation period of the heating element to modulate the IR beam at time T=1.

In FIG. 6, at the end of the translation period, the modulatable infrared emitter 1 has translated back to the right, to the starting point of the movement. The heatable regions 9 are again in the first position, just below the non-transmissive regions 15. The unmodulated radiation 29 is essentially absorbed and/or reflected and the intensity of the IR beam is minimal. Now a new translation period can start anew with the same sequence. The end time of the shown period coincides with the start time of the following period.

In a traversed translation period, as shown in FIGS. 3-6, the first position was passed twice and two different second positions passed once. The end point of the period is assigned to the next period, whose starting point it represents. Thus, the intensity was twice minimum and maximum within one translation period. At a translation frequency of f, the IR beam is thus modulated with an average frequency of about 2·f.

It is noted that various alternatives to the described embodiments of the invention may be used to carry out the invention and arrive at the solution according to the invention. Thus, the infrared emitter according to the invention, the system, and methods and uses thereof are not limited in their embodiments to the foregoing preferred embodiments. Rather, a multitude of embodiments is conceivable, which may deviate from the solution presented. The aim of the claims is to define the scope of protection of the invention. The scope of protection of the claims is directed to covering the infrared emitter according to the invention, the system, methods of their use as well as equivalent embodiments thereof.

LIST OF REFERENCE SIGNS 1 modulating infrared emitter
3 aperture structure
5 structured micro-heating element
7 actuator
9 heatable regions
10 first state
11 non-heatable regions
12 second state
13 transmissive (transparent) regions
15 non-transmissive (opaque) regions
17 heating lamella
18 housing
19 support
21 cover element
23 side parts
25 sealing elements
27 lens
29 unmodulated radiation

The invention claimed is:

1. A modulatable infrared emitter comprising
an aperture structure,
a structured micro-heating element and
an actuator,
wherein the micro-heating element exhibits in a first plane heatable and non-heatable regions, the aperture structure exhibits in a second plane transmissive regions and non-transmissive regions for infrared radiation, the two planes being parallel to one another, the aperture structure and the micro-heating element are movable in the parallel planes relative to each other, and the actuator is configured for a relative movement of the aperture structure and the micro-heating element between at least a first and a second position, such that an extinction ratio of at least 2 is achievable for the infrared radiation emittable by the micro-heating element through the aperture structure between the first and second position, wherein in the first position the IR radiation emittable by the heatable regions is predominantly absorbed and/or reflected by the non-transmissive regions of the aperture structure, while in the second position the IR radiation emittable by the heatable regions predominantly radiates through the transmissive regions of the aperture structure.

2. The modulatable infrared emitter according to claim 1, wherein the actuator is coupled to the heating element and is configured for translational movement of the heating element relative to the aperture structure, or the actuator is coupled to the aperture structure and is configured for translational movement of the aperture structure relative to the heating element.

3. The modulatable infrared emitter according to claim 1, wherein the infrared emitter comprises a housing in which the aperture structure, the micro-heating element and the actuator are installed.

4. The modulatable infrared emitter according to claim 1, wherein the micro-heating element comprises a substrate on which at least partially a heatable layer of a conductive material is deposited, on which contacts for a current and/or voltage source are present.

5. The modulatable infrared emitter according to claim 1, wherein the micro-heating element comprises a lamellar structure, a meander structure and/or a grid structure.

6. The modulatable infrared emitter according to claim 1, wherein the actuator is a MEMS actuator.

7. The modulatable infrared emitter according to claim 1, wherein the non-transmissive regions of the aperture structure exhibit a transmittance of less than 0.1 in a wavelength range within 780 nm to 1 mm and the transmissive regions of the aperture structure exhibit a transmittance of more than 0.9.

8. The modulatable infrared emitter according to claim 1, wherein the infrared emitter comprises a housing in which the aperture structure, the micro-heating element and the actuator are present installed, wherein the aperture structure is thermally decoupled from the housing or wherein the housing comprises a cover element in which the aperture structure is present fixated and at least one optical filter is additionally installed in the cover element.

9. The modulatable infrared emitter according to claim 1, wherein with respect to the possible relative movement between the micro-heating element and the aperture structure, in the first plane the heatable regions and non-heatable regions of the micro-heating element and in the second plane the transmissive regions and non-transmissive regions of the aperture structure are arranged periodically.

10. The modulatable infrared emitter according to claim 1, the actuator is a MEMS actuator selected from the group comprising electrostatic actuator, piezoelectric actuator, electromagnetic actuator.

11. The modulatable infrared emitter according to claim 1, the actuator is an electrostatic MEMS actuator in the form of a comb drive based on a variation of the comb overlap and/or the comb spacing.

12. A manufacturing method for an infrared emitter according to claim 1, wherein the manufacture of the micro-heating element comprises the following steps:
etching of the substrate;
deposition of a conductive material on the substrate;
optionally, patterning the conductive material to form a heatable layer; and
contacting the conductive material.

13. The manufacturing method according to claim 12, wherein etching and/or patterning is selected from the group consisting of dry etching, wet chemical etching, plasma etching, reactive ion etching, and reactive ion deep etching (Bosch process); or the deposition is selected from the group consisting of physical vapor deposition (PVD), thermal evaporation, laser beam evaporation, arc evaporation, molecular beam epitaxy, sputtering, chemical vapor deposition (CVD) and atomic layer deposition (ALD).

14. A system comprising:
   a) a modulatable infrared emitter according to claim 1, and
   b) a control device, wherein the control device is configured for regulating the actuator for relative movement of the heating element and the aperture structure between a first and a second position.

15. The system according to claim 14, wherein the control device is configured to regulate the temperature of the heatable regions of the micro-heating element.

16. The system according to claim 14 wherein the control device is configured to regulate the actuator for an oscillating relative movement of the heating element and the aperture structure, wherein during a period of the oscillation at least a first and a second position are passed.

17. The system according to claim 14 wherein the control device is configured to regulate the actuator for an oscillating relative movement of the heating element and the aperture structure such that a modulation frequency of the radiant power of the emitted infrared radiation between 10 Hz and 100 kHz is achieved.

18. A method for a modulated emission of infrared radiation comprising:
   providing a modulatable infrared emitter according to claim 1;
   heating the heatable regions of the micro-heating element to emit an infrared radiation; and
   controlling the actuator for relative movement of the aperture structure and the micro-heating element between at least a first position and a second position to modulate the radiant power of the emitted infrared radiation.

19. A method of performing photoacoustic spectroscopy and/or infrared spectroscopy comprising using a modulatable infrared emitter according to claim 1.

20. A photoacoustic spectroscope for the analysis of gas, comprising:
   a modulatable infrared emitter according to claim 1,
   an analysis volume fillable with gas, and
   an acoustic detector,
   wherein the analysis volume is positioned between the infrared emitter and the acoustic detector so that the infrared radiation modulatably emitted by the infrared emitter can be used for photoacoustic spectroscopy of the gas.

* * * * *